US008200449B2

(12) United States Patent
Mark

(10) Patent No.: US 8,200,449 B2
(45) Date of Patent: *Jun. 12, 2012

(54) TESTING LINEARITY OF METHODS OF CHEMICAL ANALYSIS WITH VARIOUS STATISTICAL TESTS

(76) Inventor: Howard L. Mark, Suffern, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/190,178

(22) Filed: Jul. 25, 2011

(65) Prior Publication Data

US 2011/0282628 A1    Nov. 17, 2011

Related U.S. Application Data

(60) Division of application No. 10/919,744, filed on Aug. 17, 2004, now Pat. No. 8,095,329, which is a continuation-in-part of application No. 10/365,220, filed on Feb. 12, 2003, now Pat. No. 6,795,785.

(60) Provisional application No. 60/357,912, filed on Feb. 19, 2002.

(51) Int. Cl.
G06F 19/00    (2011.01)
G01D 18/00    (2006.01)

(52) U.S. Cl. ............... 702/86; 435/6; 435/14; 702/20; 702/22

(58) Field of Classification Search ............ 702/19, 702/20, 22, 32, 86; 435/6, 7.1, 7.2, 14
See application file for complete search history.

(56) References Cited

U.S. PATENT DOCUMENTS

| 6,188,969 | B1 | 2/2001 | Minor |
| 6,415,233 | B1 | 7/2002 | Haaland |
| 6,453,243 | B1 | 9/2002 | Watanabe et al. |
| 6,795,785 | B2 * | 9/2004 | Mark ............... 702/86 |

OTHER PUBLICATIONS

Anscombe, F.J.; Amer. Stat.; 27 p. 17-21 (1973).
Durbin, J.; Biometrika; An Alternative to the Bounds Test for Testing for Serial Correlation in Least-Squares Regression; 38 p. 422-429 (1970).
Arden, B.W.; "An Introduction to Digital Computing"; 1st ed; Addison-Wesley Publishing Co., Inc.; Reading, Mass. (1963).
Draper, N., Smith, H.; "Applied Regression Analysis"; 3 ed; John Wiley & Sons; New York (1998).
Hart, W.L.; "Brief College Algebra"; D.C. Heath & Co.; Boston (1947).
Mandel, J.; "Evaluation and Control of Measurements"; Marcel Dekker, Inc.; New York (1991).
Daniel, C., Wood, F.; "Fitting Equations to Data—Computer Analysis of Multifactor Data for Scientists and Engineers"; 1 ed; John Wiley & Sons; (1971).
ICH-Q2A; "Guideline for Industry: ICH-Q2A, Text on Validation of Analytical Procedures" FDA: Rockville, Maryland (Mar. 1, 1995).
Dixon, W.J., F.J. Massey, J.; Introduction to Statistical Analysis; 4th ed; McGraw-Hill; New York (1983).
Ritchie, G.E., Roller, R.W., Ciurczak, E.W., Mark, H., Tso, C., MacDonald, S.A.; Journal of Pharmaceutical and Biomedical Analysis; 29 (1-2), p. 159-171(2002).
Ritchie, G.E., Roller, R.W., Ciurczak, E.W., Mark, H., Tso, C., MacDonald, S.A.; Journal of Pharmaceutical and Biomedical Analysis; 28 (2), p. 251-260 (2002).
Mark, H.; NIR News: 13 (3), p. 12-14 (2002).
Mark, H.; "Principles and Practice of Spectroscopic Calibration"; John Wiley & Sons; New York (1991).
Taylor, J.K.; "Quality Assurance of Chemical Measurements": Lewis Publishers; Chelsea, Michigan (1987).
Meier, P.C., Zund, R.E. "Statistical Methods in Analytical Chemistry"; John Wiley & Sons; New York (1992).
Hald, A.; "Statistical Theory with Engineering Applications"; John Wiley & Sons, Inc.; New York (1952).
Durbin, J., Watson, G.S., Biometrika; Testing for Serial Correlation in Least Squares Regression, I; 37 p. 409-428 (1950).
Durbin, J., Watson, G.S.; Biometrika; Testing for Serial Correlation in Least Squares Regression, II; 38 p. 159-178 (1951).
Durbin, J., Watson, G.S.; Biometrika; Testing for Serial Correlation in Least Squares Regression, III; 58 p. 1-19 (1971).
Durbin, J.; Biometrika: Tests for serial correlation in regression analysis based on the, periodogram of least-squares residuals; 56 p. 1-15 (1969).

* cited by examiner

*Primary Examiner* — John H Le
(74) *Attorney, Agent, or Firm* — St. Onge Steward Johnston & Reens LLC

(57) ABSTRACT

A method for testing the linearity or non-linearity of an actual analyte concentration and a test result, where the actual concentration of the analyte and a test result are determined so that a computation based upon an algorithm may be performed, which allows computation of various variables so that regression may be performed and the linear significance may be determined.

11 Claims, No Drawings

TESTING LINEARITY OF METHODS OF CHEMICAL ANALYSIS WITH VARIOUS STATISTICAL TESTS

CROSS-REFERENCE TO RELATED APPLICATIONS

This patent application is a divisional of currently pending U.S. patent application Ser. No. 10/919,744 filed on Aug. 17, 2004, which in turn is a continuation-in-part of U.S. patent application Ser. No. 10/365,220 filed on Feb. 12, 2003, now U.S. Pat. No. 6,795,785 issued on Sep. 21, 2004, which claims the benefit under 35 U.S.C. §119(e) of the U.S. Provisional Patent Application Ser. No. 60/357,912 filed on Feb. 19, 2002. All prior applications are herein incorporated by reference.

FIELD OF THE INVENTION

A testing method for an analyte concentration and a test result, where a concentration of the analyte and the test result are computed in connection with an algorithm for computation of various variables so that a linear significance may be determined.

BACKGROUND OF THE INVENTION

The Food and Drug Administration ("FDA") sets guidelines for testing methods utilized in the pharmaceutical and related industries. The FDA evaluates whether a particular analytical method is suitable for its intended purpose. Once it is established that the method is suitable, the method is "validated."

In order to validate a testing method, the FDA requires an applicant to evaluate many differing characteristics of the method. Although not all the characteristics of a particular method must be demonstrated in each case, the linearity of the relationship between an actual analyte concentration and a test result from the method is required for all quantitative methods.

Linearity is independent of the technology used to ascertain the analyte concentration. For instance, even the most modern instrumental methods that rely on multivariate chemometric computer methods have to produce a number that represents a final answer for the analyte, which would be the test result from the instrument. Therefore, the term "linearity" applies to all types of analytical methodology from manual wet chemistry to the latest high-tech instrument.

The FDA guidelines provide various definitions of the meaning of the term "linearity". For instance, one definition is: " . . . ability (within a given range) to obtain test results which are directly proportional to the concentration (amount) of analyte in the sample." This is a definition that is essentially unattainable in practice when noise and error are taken into account. For instance, a set of hypothetical data points that most would agree represents a substantially linear relationship between a test result and an analyte concentration may be plotted. However, even though there is a line that meets the criterion that "test results are directly proportional to the concentration of analyte in the sample", none of the data points may actually fall on the line. Therefore, based upon the FDA definition, none of the data points representing the test results can be said to be proportional to the analyte concentration.

Differing descriptions of linearity are also provided. For instance, one recommendation is visual examination of a plot (unspecified, but presumably also of the method response versus the analyte concentration). Because this method requires a visual examination, it is inherently subjective and not amenable to the application of statistical tests, making an objective mathematical evaluation unattainable. This method is also open to different interpretations, and is unsuitable for application with computerized or automated screening methods.

A further recommendation in the guidelines is to use "statistical methods"; where calculation of a linear regression line is advised. This however, is not so much a definition of linearity, as an attempt to evaluate linearity. For instance, if regression is performed, then the correlation coefficient, slope, y-intercept and residual sum of squares are determined. However, there are no guidelines as to how these quantities are to be related to linearity. One reference by F. J. Anscombe, Amer. Stat. 27 pp. 17-21, presents several (synthetic) data sets, which are fit to a straight line using Least Squares regression. One data set is substantially linear, while another is a data set that is non-linear. However, when linear regression is performed on any of these data sets as recommended by the guidelines, all the recommended regression statistics are identical for the sets of data. It is immediately observed that the linear regression results cannot distinguish between the two cases, since the regression results are the same for both of them.

Other linearity tests exist, in addition to the ones in official guidelines. One such proposed test is the Durbin-Watson ("DW") statistic, for use as a statistically based test method for evaluating linearity. However, it has been determined that use of the DW statistic provides unsatisfactory results. For instance, DW for residuals from regression data that are random, independent, normally distributed and represent a linear relation between two variables has an expected value of two. (See Draper, N., Smith, H., "Applied Regression Analysis" 3 ed., John Wiley & Sons, New York (1998) pp. 180-185). However, a fatal flaw in the DW method for use in this regard may be shown by calculating the DW statistic for the data sequence: 0, 1, 0, −1, 0, 1, 0, −1, 0, 1, 0, −1, . . . which, also results in a computed value of two, despite the fact that this sequence is non-random, non-independent, not normally distributed and not linear. Sets of residuals showing a similar cyclic behavior also compute out to a value of DW that will erroneously indicate satisfactory behavior of the residuals.

Another test is a statistical F-test. An F-test is based on comparing sample estimates to the overall error of the analysis. This test is undesirable because it is insensitive. For instance, any bias in the estimates of the concentration will inflate the F-value, which will be taken as an indicator of non-linearity when some other phenomenon may be affecting the data. Furthermore it requires multiple readings of every sample by both the method under test and the method used to determine the actual concentration of the analyte, making it impractical to apply on a routine basis, and inapplicable to already existing data.

Still another method is disclosed by Hald, A., "Statistical Theory with Engineering Applications", John Wiley & Sons, Inc. New York (1952). Hald recommends testing whether the residuals are normally distributed since it is unlikely that the residuals will be normally distributed if there is appreciable non-linearity in the relationship between concentration and the test results. However, this test is again insensitive to actual non-linearity (especially for small numbers of samples), and also suffers from the same difficulties as the F-test, namely that other types of problems with the data may be erroneously called non-linearity.

None of the above-mentioned methods are completely satisfactory for utilization in the pharmaceutical and related industries. In fact, the recommendations of the official guidelines for evaluating linearity, both the definitions and the recommended method(s) for assessing it are themselves not suitable for their intended purpose.

Therefore what is desired is to provide a new method for reliably testing the linearity of data.

It is further desired to provide statistical results that the current FDA test procedure recommends in a context that makes those statistics more meaningful.

It is further desired to provide the derivation and details of the operation for the new method of evaluating data.

It is also desired to disclose a report on the ability of the new method to test linearity by applying it to data from a real analytical method.

It is further desired to disclose a report on the ability of the new method to test linearity of Near Infra-Red ("NIR") spectroscopic analysis using diffuse transmittance measurements.

It is still further desired to disclose a report on the ability of the new method to test linearity of NIR spectroscopic analysis using diffuse reflectance measurements.

SUMMARY OF THE INVENTION

A method of determining non-linearity (or showing linearity) is proposed here by fitting a straight line to the data and assessing the fit. But as shown, the currently recommended method for assessing linearity is faulty because it cannot distinguish linear from non-linear data.

Examination of the requirements of the FDA for evaluating the linearity of an analytical method reveals them to be unsatisfactory, in both the definition of linearity and in the specifications for testing this property of an analytical method. Therefore, we first define linearity as follows; linear data is: "data where the relationship between analyte concentrations and test results can be fitted (in the Least-Squares sense) as well by a straight line as by any other function."

When examining the proposed definition of linearity, this method may seem to be similar to the FDA approach. However, the difference is that this new method includes fitting other functions to the data and comparing the fits, whereas the FDA guidelines only specify trying to fit a straight line to the data. This new method is also compatible with the proposed definition of linearity because functions other than a straight line are compared to the data, and if an improved fit is not obtained, it is concluded that the data is linear.

It is possible to fit other functions to a set of data, using least-squared mathematics. In fact, the Savitzky-Golay ("S-G") algorithm is based on fitting polynomials to data. However, this new method differs from the S-G method in that, while S-G fits a polynomial to small sections of the data, we fit the polynomial to the entire data set simultaneously, rather than a few data points at a time.

For the new method, data is assumed to be univariate and to follow the form of some mathematical function, although the nature of the function may be undetermined. From Taylor's theorem, however, any function may be approximated by a polynomial, although the degree of the polynomial may also not be known a priori (the "degree" of a polynomial being the highest power to which the variable is raised in that polynomial).

Based upon the forgoing, we do not need to approximate the relationship between test results and analyte concentration as accurately as possible, but rather, we need only ascertain whether a straight line fits the data as well as a polynomial. To accomplish this, it has been determined that it is not necessary to utilize polynomials of high degree.

Accordingly, in one advantageous embodiment of the present invention, a method for determining the linearity of data points is provided comprising the steps of ascertaining an actual concentration (Y) of a sample of an analyte and measuring the sample to generate a result (X). The method further comprises the steps of computing a value of Z from the following formula:

$$Z = \frac{\sum_{i=1}^{N} X_i^2 (X_i - \overline{X})}{2 \sum_{i=1}^{N} X_i (X_i - \overline{X})}$$

and computing a new variable $(X-Z)^2$ from each value of X. The method still further comprises the steps of regressing X and $(X-Z)^2$ against Y to generate coefficients having t-values and evaluating the t-values of the coefficients of X and $(X-Z)^2$, to determine if the linear term exceeds a threshold value to determine if nonlinearity exists. It should be noted however and a number of various alternative statistical tests rather than the T-test may effectively be utilized. Some of the alternative statistical tests include for instance, a partial F-value and a P-value. The partial F-test (sometimes called an "F to delete" or an "F to remaove") is described in "Applied Regression Analysis" $3^{rd}$ edition, by Draper, N. R. and Smith, H., pp. 339-42 published by John Wiley & Sons (1981).

The T-value and the partial F-test are both ways to calculate the probability (p) for the corresponding regression coefficient. In some cases, the probability is calculated and presented directly by, for instance, a software program. This may be known as a P-test, the probability for the corresponding coefficient.

In another advantageous embodiment a method for determining the linearity of data points is provided comprising the steps of ascertaining an actual concentration (Y) of a sample of an analyte and measuring the sample to generate a result (X). The method further comprises the steps of computing Z from the following formula:

$$Z = \frac{\sum_{i=1}^{N} X_i^2 (X_i - \overline{X})}{2 \sum_{i=1}^{N} X_i (X_i - \overline{X})}$$

and computing a new variable $(X-Z)^2$ from each value of X. The method still further comprises the steps of regressing X and $(X-Z)^2$ against Y as a multiple regression analysis utilizing an Inverse Least Squares algorithm to generate coefficients having t-values and evaluating the t values of the coefficients of X and $(X-Z)^2$, to determine if the linear term exceeds a threshold value to determine if nonlinearity exists. While calculation of a t-value is illustrated, it should be noted that a partial F-value and a P-value may also effectively be used.

In still another advantageous embodiment a method for determining the linearity of data points is provided comprising the steps of determining an actual concentration of a sample of an analyte and generating concentration data and testing the sample and generating test data. The method further comprises the steps of comparing the concentration data to the test data to generate related data, fitting a non-linear function to the related data, and fitting a straight line to the related data. Finally, the method further comprises the step of determining whether the straight line fits the related data as well as the non-linear function and concluding that the related data is linear when the straight line fits the related data as well as the non-linear function.

In yet another advantageous embodiment a method for determining the linearity of data points is provided comprising the steps of generating concentration data of a sample, testing the sample to generate test data, and computing the concentration data with the test data to generate coefficients having values. The method further comprises the steps of fitting a non-linear function to the coefficients, fitting a linear function to the coefficients, and determining whether the straight fits the related data as well as the non-linear function so as to access linearity.

The invention and its particular features and advantages will become more apparent from the following detailed description considered with reference to the accompanying drawings.

DETAILED DESCRIPTION OF THE INVENTION

The new linearity testing method utilizes various mathematical formulations, the derivations of which are outlined below.

The first assumption made is that there is a single (univariate) mathematical system (corresponding to "analyte concentration" and "test reading"), and that there is a functional relationship between these two variables of interest, although the nature of the relationship may be unknown. The function is approximated by a polynomial, and any given polynomial must minimize the sum of the squares of the differences between each datum and the corresponding point of the polynomial.

The easiest type of polynomial to deal with, and therefore the most widely used for approximating functions are simple polynomials; these are also convenient in that they are the direct result of applying Taylor's theorem, since Taylor's theorem produces a description of a polynomial that estimates the function being reproduced:

$$Y = a_0 + a_1 X + a_2 X^2 + a_3 X^3 + \ldots a_n X^n \quad \text{(Equation 1)}$$

where X and Y correspond to the test results and the analyte concentrations. Often a polynomial of degree 2 (quadratic) can provide a satisfactory fit to the data. Polynomials of higher degree may provide a better fit, if the data requires it.

The mathematics of fitting a polynomial by least squares are relatively straightforward, and we sketch the derivation. But as we shall see, this is rather generic: Starting from equation 1, we want to find coefficients (the $a_i$) that minimize the sum-squared difference between the data and the function's estimate of that data, given a set of values of X. Therefore we first form the desired differences:

$$D = a_0 a_1 X + a_2 X^2 + a_3 X^3 + \ldots + a_n X^n - Y \quad \text{(Equation 2)}$$

Then we square those differences and sum those squares over all the sets of data (corresponding to the samples used to generate the data):

$$\Sigma_i D^2 = \Sigma_i (a_0 + a_1 X + a_2 X^2 + a_3 X^3 + \ldots + a_n X^n - Y)^2 \quad \text{(Equation 3)}$$

The problem now is to find a set of values for the $a_i$ that minimizes $\Sigma D^2$. This is accomplished by taking the derivative of $\Sigma D^2$ with respect to each $a_i$ and setting each of those derivatives equal to zero. Note that since there are n+1 different $a_i$ (including $a_0$), we wind up with n+1 equations, although here we only show the first three of the set.

$$\partial(\Sigma_i D^2)/\partial a_0 = \partial(\Sigma(a_0 + a_1 X + a_2 X^2 + a_3 X^3 + \ldots + a_n X^n - Y)^2)/\partial a_0 = 0 \quad \text{(Equation 4a)}$$

$$\partial(\Sigma_i D^2)/\partial a_1 = \partial(\Sigma(a_0 + a_1 X + a_2 X^2 + a_3 X^3 + \ldots + a_n X^n - Y)^2)/\partial a_1 = 0 \quad \text{(Equation 4b)}$$

$$\partial(\Sigma_i D^2)/\partial a_2 = \partial(\Sigma(a_0 + a_1 X + a_2 X^2 + a_3 X^3 + \ldots + a_n X^n - Y)^2)/\partial a_2 = 0 \quad \text{(Equation 4c)}$$

Taking the indicated derivative of each term (noting that $\partial(\Sigma_i F^2) = 2 \Sigma_i F \partial F$ (where F is the inner summation of the $a_i$ X)), separating the summations, dividing by two to eliminate the constant term and subtracting the term involving Y from each side of the resulting equations puts the equations in their final form. Here we show the result:

$$a_0 \Sigma(1) + a_1 \Sigma_i X + a_2 \Sigma_i X^2 + a_3 \Sigma_i X^3 + \ldots + a_n \Sigma_i X^n = \Sigma_i Y \quad \text{(Equation 5a)}$$

$$a_0 \Sigma_i X + a_1 \Sigma_i X^2 + a_2 \Sigma_i X^3 + a_3 \Sigma_i X^4 + \ldots + a_n \Sigma_i X^{n+1} = \Sigma_i XY \quad \text{(Equation 5b)}$$

$$a_0 \Sigma_i X^2 + a_1 \Sigma_i X^3 + a_2 \Sigma_i X^4 + a_3 \Sigma_i X^5 + \ldots + a_n \Sigma_i X^{n+2} = \Sigma_i X^2 Y \quad \text{(Equation 5c)}$$

The values of X and Y are known, since they constitute the data. Therefore equations 5a, 5b and 5c comprise a set of n+1 equations in n+1 unknowns, the unknowns being the various values of the $a_i$ since the summations, once evaluated, are constants. Therefore, solving equations 5a, 5b and 5c as simultaneous equations for the $a_i$ results in the calculation of the coefficients that describe the polynomial (of degree n) that best fits the data.

In principle, the relationships described by equations 5a, 5b and 5c could be used directly to construct a function that relates test results to sample concentrations. In practice it has been determined that correlation between the various powers of X is an important consideration that must be taken into account. For example, the correlation coefficient of the integers from 1 to 10 with their squares is 0.974, which is a rather high value.

Correlation effects are of concern for us because a goal is to formulate a method of testing linearity in such a way that the results can be justified statistically. Ultimately statistical testing will be performed on the coefficients of the fitting function utilized. A t-test is utilized to determine whether any given coefficient is statistically significant, compared to the standard error of that coefficient. It is unnecessary however, to solve the general problem. In the broadest sense, equation 1 is the basis for computing the best-fitting function to a given set of data, but that is not the goal. Rather, the goal is to determine whether the data represent a linear function or not. To this end it suffices to simply ascertain whether the data can be fit better by any polynomial of degree greater than 1, than it can by a straight line (which itself is a polynomial of degree 1). To this end, a polynomial of degree higher than 1 must be tested. While in some cases, the use of more terms may be warranted, it is generally sufficient to test using only one term of degree greater than one. Hence, while in general it may be desirable to try fitting equations of degrees 3, 4, ... m (where m is some upper limit less than n), we need begin by using only polynomials of degree 2, i.e., quadratic fits.

A complication arises however, caused by the correlation effects. It is determined from considerations of multiple regression analysis, that when two (or more) variables are correlated, the standard error of both variables is increased over what would be obtained if equivalent but uncorrelated variables are used. For instance, the variance of the estimates of coefficients (from their standard errors) is increased by a factor of:

$$VIF = 1/(1-R^2) \quad \text{(Equation 6)}$$

when there is correlation between the independent (X) variables, where R represents the correlation coefficient between the variables and we use the term VIF, to mean Variance Inflation Factor. A general method for removing the correlation between the various powers of X in a polynomial, based on the use of orthogonal Chebyshev polynomials is described by Arden. Arden, B. W.; "An Introduction to Digital Computing"; 1$^{st}$ ed.; Addison-Wesley Publishing Co., Inc.; Reading, Mass. (1963). Other types of orthogonal polynomials also exist and could be used, such as Legendre polynomials, Jacobi polynomials, and others.

This method however, is unnecessarily complicated and in any case provides unsatisfactory results when applied to actual data. For instance, Chebyshev and other types of orthogonal polynomials are orthogonal only if the data is uniformly, or at least symmetrically, distributed along the X-axis; whereas in practical applications, real data will seldom meet that requirement.

Since it is unnecessary to deal with the general case, a simpler method to orthogonalize the variables can be utilized where a transformation makes the square of that variable uncorrelated with the variable itself. (See Daniel, C. Wood, F.; "Fitting Equation to Data—Computer Analysis of Multifactor Data for Scientists and Engineers"; 1 ed; John Wiley & Sons; (1971)). This may be accomplished by computing a new variable Z such that for the given data set, $(X-Z)^2$ is uncorrelated with X. Once Z is computed, it is subtracted from each of the original values of X and the result is squared. A symmetric distribution of the data is not required since the data distribution is taken into account in the formula. Z is calculated, by imposing the condition that $(X-Z)^2$ is to be uncorrelated with X, this requires that the condition:

$$\Sigma_i (X_i - \overline{X})(X_i - Z)^2 = 0 \quad \text{(Equation 7)}$$

must be met (where the summation is taken over all the samples in the set). Solving this equation for Z is not obvious; therefore it will be shown how to solve equation 7 for Z. First expand the square term in equation 7:

$$\Sigma_i (X_i - \overline{X})(X_i^2 - 2X_i Z + Z^2) = 0 \quad \text{(Equation 8)}$$

Then multiply through and collect terms:

$$\Sigma_i (X_i^2 (X_i - \overline{X}) - 2X_i Z(X_i - \overline{X}) + Z^2 (X_i - \overline{X})) = 0 \quad \text{(Equation 9)}$$

Separate the summations and bring constants outside the summations:

$$\Sigma_i X_i^2 (X_i - \overline{X}) - 2Z \Sigma_i X_i (X_i - \overline{X}) + Z^2 \Sigma_i (X_i - \overline{X}) = 0 \quad \text{(Equation 10)}$$

Since $\Sigma_i (X_i - \overline{X}) = 0$, the last term in equation 10 vanishes, leaving:

$$\Sigma_i X_i^2 (X_i - \overline{X}) - 2Z \Sigma_i X_i (X_i - \overline{X}) = 0 \quad \text{(Equation 11)}$$

Equation 11 is now easily rearranged explicitly for Z:

$$Z = \frac{\sum_{i=1}^{N} X_i^2 (X_i - \overline{X})}{2 \sum_{i=1}^{N} X_i (X_i - \overline{X})} \quad \text{(Equation 12)}$$

Thus it is shown that equation 12 provides the value of Z that causes $(X-Z)^2$ to be uncorrelated with X. Z will equal $\overline{X}$ if the data are symmetrically (or uniformly) distributed, but generally will not equal $\overline{X}$.

Creating an orthogonal variable using equation 12 provides the advantage that the data in the resulting variable is orthogonal to the original X data regardless of the distribution of the X values. This procedure can therefore be applied to a set of real data without concern for the distribution of that data.

It should also be noted that equation 12 may be converted into equation 13.

$$Z = \frac{\sum_{i=1}^{N} X_i^2 (X_i - \overline{X})}{2 \sum_{i=1}^{N} (X_i - \overline{X})^2} \quad \text{(Equation 13)}$$

Expressions corresponding to equation 7 may similarly be set up for creating terms for the third, fourth, and even higher powers of the variables that are uncorrelated to the X variable:

$$\Sigma_i (X_i - \overline{X})(X_i - Z_3)^3 = 0 \quad \text{(Equation 15A)}$$

$$\Sigma_i (X_i - \overline{X})(X_i - Z_4)^4 = 0 \quad \text{(Equation 15B)}$$

where the various $Z_i$ represent the value of Z needed to make the variable for the corresponding power of X uncorrelated with X itself. Solving each of these equations 15A and 15B for the corresponding $Z_i$ will provide a value that creates a term for the corresponding power of X that is uncorrelated with X. From equation 15A the following expression may be obtained:

$$Z_3^2 \sum_i X_i (X_i - \overline{X}) - \quad \text{(Equation 16A)}$$
$$Z_3 \sum_i X_i^2 (X_i - \overline{X}) + \frac{1}{3} \sum_i X_i^3 (X_i - \overline{X}) = 0$$

which is quadratic in $Z_3$ and may be solved by the usual formula, or by an approximation method. Application of this formula to several sets of test data followed by further study of the behavior of polynomials of odd degree (specifically, the relation between X and $X^3$) reveals that for any data that could represent actual validation data, no real roots of the equation exist; the roots of equation 16A are complex (in the sense of being of the mathematical form a+bi, where i represents the square root of −1).

Similarly, equation 15B results in the following expression, which is cubic in $Z_4$, and which can also be solved using either known algebraic methods, or approximation methods:

$$Z_4^3 \sum_i X_i (X_i - \overline{X}) - \frac{6}{4} Z_4^2 \sum_i X_i^2 (X_i - \overline{X}) + \quad \text{(Equation 16B)}$$
$$Z_4 \sum_i X_i^3 (X_i - \overline{X}) - \frac{1}{4} \sum_i X_i^4 (X_i - \overline{X}) = 0$$

Since equation 16B is cubic in $Z_4$, it is guaranteed to have at least one real root, and linearity testing can proceed. Arguing by induction, it may be concluded that polynomials of even degree are amenable to this procedure, while polynomials of odd degree are not. However, this consideration is moot, even though similar expressions may be generated to correspond to higher powers of X, to create corresponding variables for powers of X that are uncorrelated to X.

While $Z_4$ is not necessarily orthogonal to Z, it is orthogonal to the data (X), and so will all powers of $(X-Z_i)$ be orthogonal to X. Therefore, each one could be tested separately, for as many terms as are needed to make up a polynomial of the desired degree. Should it become necessary to evaluate non-linearity terms that are represented by higher powers of X, they need not be evaluated simultaneously, each variable: $(X-Z)^2$, $(X-Z_4)^4$, etc. can each be evaluated separately, preventing possible intercorrelations between the $Z_i$ from influencing the results.

Taylor's theorem tells that, while any function may be approximated by a polynomial, the terms of a Taylor expansion results in coefficients of the polynomials that necessarily decrease for higher powers of the polynomial due to the presence of n! in the denominator of the Taylor formula (where n represents the power of any given term). Therefore, Taylor's theorem teaches that it is unusual to have to go beyond the quadratic term. That being the case, the issue of orthogonality of terms, as well as the problem of polynomials of odd degree; all become moot. Testing data for quadratic non-linearity will suffice to reveal the presence of any non-linearity in the data.

At this point we note that equation 7, and indeed the whole derivation leading to it is familiar to us, in a different context. In using spectroscopy to do quantitative analysis, we use an equation for a calibration model similar to equation 1 to express Beer's Law; one of the representations of the equation involved is:

$$C = b_0 + b_1 X_1 + b_2 X_2 + \ldots b_n X_n \quad \text{(Equation 17)}$$

Equation 17 is commonly used to represent the equations needed for doing quantitative spectroscopic analysis using what is called the Multiple Linear Regression ("MLR") algorithm (also sometimes called P-matrix or Inverse Least Squares). The various $X_i$ in equation 17 represent entirely different variables, in spectroscopic analysis they are absorbances at different wavelengths. Nevertheless, starting from equation 17, the set of equations for calculating the MLR calibration coefficients may be derived in the same way equation 7 from equation 1 was derived. Comparison of the derivations with equations 1-7 is instructive as they are parallel and therefore, the following equivalencies may be utilized:

$$b_0 = a_0$$

$$b_1 = a_1 X_1 = X$$

$$b_2 = a_2 X_2 = (X-Z)^2$$

$$b_4 = a_4 X_4 = (X-Z_4)^4$$

and it is shown that by using X, $(X-Z)^2$, $(X-Z_4)^4$, etc., for the MLR variables $X_1$, $X_2$, $X_4$, etc. respectively, common and well-understood statistical methods (and computer programs) of multiple regression analysis may be utilized to perform the necessary calculations. A consideration of key importance is that, along with the values of the coefficients of the various powers of X, all the common statistical estimates; of variances, of standard errors, of goodness of fit, etc. that computer programs produce for us along with the ones specified by the FDA, may be obtained. Of special interest is the fact that many programs compute estimates of the standard errors of the coefficients. This facilitates testing of the statistical significance for each of the coefficients, which are now the coefficients of the various powers of X that comprises the polynomial that is being fit to the data.

This is the basis of the new test for non-linearity. Because it not our goal to fit the data as well as possible, it is unnecessary to use polynomials of high degree. Especially since it is anticipated that well-behaved methods of chemical analysis will produce results that are already close to being linearly related to the analyte concentrations, it is therefore expected that non-linear terms will decrease as the power of X increases. Thus it is only necessary to test the fit of a quadratic equation to the data to test for linearity, although there is no impediment from testing equations of higher degree if so desired. Data that is well described by a linear equation will produce a set of coefficients with a statistically significant value for the term $X^1$ (which equals X), and will produce small, statistically non-significant values for the coefficients of the variables representing $X^2$ or higher powers of X.

One method for performing the test is disclosed as follows:
1) Ascertain the actual concentration (Y) of the analyte and measure the test result (X);
2) Compute Z from the test results according to equation 12;
3) Compute the new variable $(X-Z)^2$ from each value of X;
4) Regress X and $(X-Z)^2$ against Y, using an MLR program that computes the desired statistics (it is required that at least one of the t-value, the partial F-value or the P-value for the coefficients is included among these statistics);
5) Inspect the t statistic of the coefficients of X and $(X-Z)^2$, to determine if the linear term is statistically significant and whether the t-value for the coefficient of $(X-Z)^2$ indicates statistical significance; if so, that indicates that statistically significant nonlinearity exists. Alternatively, it should be noted that a partial F-value and a P-value may be used instead of a t-value.

This test procedure has several advantages. First, it provides an objective, unambiguous determination, based on standard statistical methodology, of whether any non-linearity is present in the relationship between the test results and analyte concentration. Since the test procedure is based on regression analysis, it is a straightforward extension of the current method specified by the FDA. Second, the test procedure provides a means of distinguishing between different types of non-linearity, if present, since only those that have statistically significant coefficients are active. Third, the test procedure is more sensitive than the DW statistic, and is also immune to the fatal flaw that afflicts DW with regard to cyclic behavior. Because of the extreme variability of DW for small numbers of samples, standard tables for the thresholds of the DW statistic only give values for more than 10 samples. However, because this new method of linearity testing depends on calculating the t value rather than comparing variances, it is applicable to data from fewer than 10 samples.

Analysis of samples may be accomplished utilizing Near Infra-Red ("NIR") spectroscopy. However, since analysis using NIR spectroscopy requires that samples have their concentrations measured using a method of known accuracy to provide reference values, the reference values for samples should be measured using already validated High Performance Liquid Chromatography ("HPLC") methods appropriate for each sample type.

Experimental Results. The following is an experiment conducted utilizing the new method for testing linearity.

Two groups independently devised nearly identical measurement protocols to validate analytical methods for similar sample types. FOSS/NIR Systems model 6500 NIR spectrometers, each fitted with Intact™ tablet analyzer modules were used to collect transmittance spectra of the samples. The first group measured tablets, while the second group measured capsules. The difference between the experimental setups was that each group used a sample mask specific to their samples. A standard default value of 32 scans was used for collecting each spectrum.

Since analysis using NIR spectroscopy requires that the samples have their concentrations measured using a method of known accuracy to provide reference values, the reference values for the samples used in this study were measured using already validated HPLC methods appropriate for each sample type. In addition, all calculations were performed using programs written in MATLAB™.

For the tablet study, 96 samples were utilized for calibration, and 42 samples were used as an independent test set.

For the capsule study, 70 samples were utilized for calibration, and 21 samples were used as an independent test set.

All sets of data appear satisfactorily linear. The plot of the test data for the capsule product reveals that the range of the values for the test samples is extremely limited. As will be seen, this affects the statistics that are computed for this data, especially the correlation coefficient. In a previous study, the DW statistic also was computed to assess linearity; the conclusion of that test also indicated that there was no evidence of non-linearity.

However, Tables 1 and 2 present the results of applying the new linearity test to the tablet product and the capsule product, respectively. The test was applied separately to the calibration data, and to the test data for each product. For comparison purposes, a straight line was also fitted to each data set. For this example only a t-value was calculated in order to test the linearity of the data, however, as mentioned above, a partial F-value or a P-value may also effectively be utilized.

TABLE 1 the results of testing the linearity of the data from the tablet product.

| Parameter | Coefficient when using only linear term | t-value when using only linear term | Coefficient including quadratic term | t-value including quadratic term |
|---|---|---|---|---|
| Results for calibration data | | | | |
| Constant | 0.000 | | −0.3376 | |
| Linear term | 1.0000 | 85.62 | 1.0000 | 86.4 |
| Square term | — | — | 0.0007 | 1.67 |
| S.E.E | 2.42 | | 2.39 | |
| R | 0.9937 | | 0.9938 | |
| Results for test data | | | | |
| Constant | 2.37 | | 2.53 | |
| Linear term | 0.9917 | 52.3 | 0.9917 | 51.92 |
| Square term | — | — | −0.0004 | −0.693 |
| S.E.E | 2.24 | | 2.26 | |
| R | 0.9928 | | 0.9928 | |

TABLE 2 the results of testing the linearity of the data from the capsule product.

| Parameter | Coefficient when using only linear term | t-value when using only linear term | Coefficient including quadratic term | t-value when including quadratic term |
|---|---|---|---|---|
| Results for calibration data | | | | |
| Constant | −0.0022 | | 0.0434 | |
| Linear term | 1.0000 | 129.7 | 1.0000 | 128.8 |
| Square term | — | — | −0.0001 | −0.175 |
| S.E.E | 1.90 | | 1.92 | |
| R | 0.9980 | | 0.9980 | |
| Results for test data | | | | |
| Constant | 90.19 | | 90.39 | |
| Linear term | 0.3986 | 6.26 | 0.3988 | 6.3213 |
| Square term | — | — | −0.0359 | −2.14 |
| S.E.E | 2.11 | | 2.09 | |
| R | 0.3986 | | 0.4209 | |

It can be seen that in all cases, the linear term of the regression is statistically significant, and except for the test set for the capsule product, where the limited range affected the results, they were all highly significant. The low value of correlation coefficient for the test set from the capsule product indicates that the limited range is the cause of the low values for all the statistics. Use of the t-value for evaluating the linear term is superior to the use of the correlation coefficient (as specified by the guidelines), because tables of critical values of t are more common and easier to evaluate than are tables of critical values for the correlation coefficient. While a t-value was used in this particular example, a partial F-value or a P-value may also have been used. Furthermore, having a known statistical value for testing the significance of the linear term provides an objective test for whether there is indeed sufficient data for making the evaluation.

In all cases it is shown that the quadratic term is non-significant, consistent with and confirming the previous results, but through the use of a test statistic that is more specific, more easily interpreted and in more common use. Having two coefficients with their corresponding t-values separates the linear from the non-linear contributions to the relationship, and yet, as a multivariate method, allows both pieces of the relationship to be tested separately but simultaneously. In this particular case, there was no reason to suspect higher-order non-linearity, but if there was, this could also be tested by including the variables corresponding to the higher-degree polynomials, as indicated by the expressions presented in equations 16A and 16B, or their obvious extensions.

As can be seen by the forgoing results, the new test of linearity can provide an objective, unambiguous decision tool as to whether a given data set exhibits non-linearity in the relationship between the test results and the analyte concentration. It also provides all the statistical results that the current FDA test procedure recommends, in a context that makes those statistics more meaningful. It also provides information as to whether, and how well, an analytical method gives a good fit of the test results to the actual concentration values. It can distinguish between different types of non-linearities, if necessary, while simultaneously evaluating the overall fit of the function.

In application to the current set of test data, it was determined that the results of using an NIR analytical method provided a linear relationship between the test result (from the NIR method) and the actual concentration of the analyte (as measured by the validated reference HPLC method).

Although the invention has been described with reference to a particular arrangement of parts, features and the like, these are not intended to exhaust all possible arrangements or features, and indeed many other modifications and variations will be ascertainable to those of skill in the art.

What is claimed is:

1. A method for determining the linearity of data points using a computer comprising the steps of:
   generating concentration data of a sample;
   testing the sample to generate test data;
   computing the concentration data with the test data to generate coefficients having values;
   fitting a non-linear function to the coefficients;
   fitting a linear function to the coefficients; and
   determining whether the linear function fits the coefficients as well as the non-linear function so as to assess linearity.

2. The method according to claim 1 wherein multiple regression analysis is used for generating the coefficients.

3. The method according to claim 2 wherein the generated coefficients have values selected from the group consisting of t-values, partial f-values or p-values.

4. The method according to claim 2 wherein the multiple regression analysis utilizes an MLR algorithm for generating the coefficients.

5. The method according to claim 2 wherein the multiple regression analysis utilizes an MLR program for computing the coefficients.

6. The method according to claim 1 wherein the step of testing the sample further comprises collecting transmittance spectra of the sample.

7. The method according to claim 6 wherein the sample is analyzed using NIR spectroscopy.

8. The method according to claim 1 wherein the step of testing the sample further comprises collecting reflectance spectra of the sample.

9. The method according to claim 8 wherein the sample is analyzed using NIR spectroscopy.

10. The method according to claim 1 wherein during the step of fitting a non-linear function to the coefficients, all of the coefficients are simultaneously fit to the non-linear function.

11. The method according to claim 1 wherein the non-linear function is a polynomial.

* * * * *